(12) United States Patent
Guerra et al.

(10) Patent No.: US 10,786,237 B2
(45) Date of Patent: Sep. 29, 2020

(54) METHODS OF MAKING REINFORCED SOFT TISSUE GRAFTS WITH SUTURE LOOP/NEEDLE CONSTRUCTS

(71) Applicant: ARTHREX, INC., Naples, FL (US)

(72) Inventors: James J. Guerra, Naples, FL (US);
Jacob A. Jolly, Naples, FL (US);
Dustin T. Libby, Naples, FL (US);
Thomas M. Deberardino, Avon, CT (US)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 16/110,041

(22) Filed: Aug. 23, 2018

(65) Prior Publication Data

US 2018/0360440 A1 Dec. 20, 2018

Related U.S. Application Data

(63) Continuation of application No. 14/845,364, filed on Sep. 4, 2015, now Pat. No. 10,448,943, which is a
(Continued)

(51) Int. Cl.
*A61B 17/04* (2006.01)
*A61F 2/08* (2006.01)

(52) U.S. Cl.
CPC ............ *A61B 17/0401* (2013.01); *A61F 2/08* (2013.01); *A61F 2/0811* (2013.01);
(Continued)

(58) Field of Classification Search
CPC ........ A61B 17/0401; A61B 2017/0414; A61B 2017/0417; A61B 2017/0404; A61F 2/08;
(Continued)

(56) References Cited

U.S. PATENT DOCUMENTS

| 4,979,956 A | 12/1990 | Silvestrini |
| 6,716,234 B2 | 4/2004 | Grafton et al. |

(Continued)

FOREIGN PATENT DOCUMENTS

| EP | 1201204 A2 | 5/2002 |
| EP | 2238944 A2 | 10/2010 |

(Continued)

OTHER PUBLICATIONS

Vidriero, E., et al "The Use of Platelet-Rich Plasma in Arthroscopy and Sports Medicine: Optimizing the Healing Environment" The Journal of Arthroscopic & Related Surgery (2010) vol. 26 (6): pp. 723-724 (Year: 2010).*
(Continued)

*Primary Examiner* — Brian A Dukert
*Assistant Examiner* — Rebecca Lynee Zimmerman
(74) *Attorney, Agent, or Firm* — Carlson, Gaskey & Olds

(57) ABSTRACT

A method of reinforcing a biological construct according to an exemplary aspect of the present disclosure includes, among other things, attaching a suture loop/needle construct to a reinforcement material and stitching the reinforcement material to a biological construct to form a reinforced biological construct. The reinforcement material is attached to the suture loop/needle construct prior to approximating the reinforcement material to the biological construct.

7 Claims, 13 Drawing Sheets

Related U.S. Application Data continuation of application No. 14/206,936, filed on Mar. 12, 2014, now Pat. No. 9,168,124.

(60) Provisional application No. 61/782,944, filed on Mar. 14, 2013.

(52) U.S. Cl.
CPC ............... *A61B 2017/0404* (2013.01); *A61B 2017/0414* (2013.01); *A61B 2017/0417* (2013.01); *A61F 2002/087* (2013.01); *A61F 2002/0852* (2013.01); *A61F 2002/0882* (2013.01); *A61F 2220/0075* (2013.01)

(58) Field of Classification Search
CPC ............ A61F 2/0811; A61F 2220/0075; A61F 2002/0852; A61F 2002/087; A61F 2002/0882
See application file for complete search history.

(56) References Cited

U.S. PATENT DOCUMENTS

| | | | |
|---|---|---|---|
| 7,238,189 B2 | 7/2007 | Schmieding et al. | |
| 7,892,256 B2 | 2/2011 | Grafton et al. | |
| 8,298,284 B2 | 10/2012 | Cassani | |
| 8,439,976 B2 | 5/2013 | Albertorio et al. | |
| 8,460,379 B2 | 6/2013 | Albertorio et al. | |
| 8,591,544 B2 | 11/2013 | Jolly et al. | |
| 2004/0254609 A1 | 12/2004 | Esplin | |
| 2007/0250163 A1 | 10/2007 | Cassani | |
| 2008/0027485 A1 | 1/2008 | Jolly et al. | |
| 2008/0046009 A1 | 2/2008 | Albertorio et al. | |
| 2009/0222039 A1* | 9/2009 | Dreyfuss ................. | A61L 27/08 606/229 |
| 2010/0203155 A1* | 8/2010 | Wei ....................... | A61F 2/4603 424/549 |
| 2010/0268273 A1 | 10/2010 | Albertorio et al. | |
| 2010/0305709 A1 | 12/2010 | Metzger et al. | |
| 2011/0125287 A1 | 5/2011 | Hotter et al. | |
| 2012/0046746 A1 | 2/2012 | Konicek | |
| 2013/0116730 A1 | 5/2013 | Denham et al. | |

FOREIGN PATENT DOCUMENTS

| | | |
|---|---|---|
| GB | 2211741 A | 7/1989 |
| WO | 2011031854 A1 | 3/2011 |

OTHER PUBLICATIONS

Extended European Search Report for Application No. EP 14 15 9454 dated Jul. 16, 2014.

Extended European Search Report for Application No. EP 17 17 2516 dated Aug. 19, 2017.

* cited by examiner

METHODS OF MAKING REINFORCED SOFT TISSUE GRAFTS WITH SUTURE LOOP/NEEDLE CONSTRUCTS

CROSS-REFERENCE TO RELATED APPLICATIONS

This application is a continuation of U.S. patent application Ser. No. 14/845,364, filed Sep. 4, 2015, which is a continuation of U.S. patent application Ser. No. 14/206,936, filed Mar. 12, 2014, now U.S. Pat. No. 9,168,124, which claims the benefit of U.S. Provisional Application No. 61/782,944, filed Mar. 14, 2013, the disclosures of which are incorporated by reference in their entirety herein.

TECHNICAL FIELD

This disclosure relates to the field of surgery and, more particularly, to suture constructs and methods of enhancing the pull out strength of soft tissue grafts.

BACKGROUND

Reconstructive surgeries, particularly tendon or ligament reconstruction, are well-known in the art. In general, these methods involve repairing a tendon or ligament by stitching it together or using a graft to repair the tendon or ligament. ACL repairs involve drilling a tunnel through the tibia, drilling a closed tunnel (socket) into the femur, inserting a substitute ACL graft into the tunnels, and securing the graft to the walls of the tibial and femoral tunnels using interference screws or the like. Tensioning and fixation of the graft in the tunnel is important for optimal results.

Repairs of other tendons or ligaments, such as the Achilles tendon, require trying to reattach the torn pieces of the existing tendon back together. This can be difficult to accomplish when the tendon ends are weaker because of the tear. The stitches can rip through the tendon at the repair site.

Attaching a fixation device such as an ACL TightRope® or button to the end of a tendon is also difficult. The graft is often too short or too thick to be folded over the fixation device. Current techniques mostly involve suturing the tendon and then tying the suture to the button. This type of fixation is dependent on the suture-tendon interface which can be too weak for certain indications such as ACL reconstruction. A "rip-stop" suturing technique is disclosed, for example, in US Publication No. 2012/0046746, entitled "Reinforced Biological Construct and Method of Reinforcing Biological Construct," the disclosure of which is incorporated in its entirety by reference herein. As detailed in US Publication No. 2012/0046746, the "rip-stop" technique can reinforce the stitching but it is difficult to use with a fixation device.

Accordingly, there is a need for simplified attachment of tendons or ligaments to fixation devices using suturing techniques such as the "rip-stop" suturing technique. Also needed are constructs that allow reinforcement of a ligament or tendon attached to a fixation device, as well as methods of reinforcing a repaired tendon or ligament at the repair site. Also needed are constructs and methods for threading suture through a tendon with maximum fixation strength, as well as methods of securing the tendon to bone that allows for accelerated tendon healing to bone.

SUMMARY

A method of reinforcing a biological construct according to an exemplary aspect of the present disclosure includes, among other things, attaching a suture loop/needle construct to a reinforcement material and stitching the reinforcement material to a biological construct to form a reinforced biological construct. The reinforcement material is attached to the suture loop/needle construct prior to approximating the reinforcement material to the biological construct.

In a further non-limiting embodiment of the foregoing method, the suture/loop needle construct comprises a needle attached to a continuous, uninterrupted suture loop.

In a further non-limiting embodiment of either of the foregoing methods, the needle is a free floating needle.

In a further non-limiting embodiment of any of the foregoing methods, the reinforcement material is selected from the group consisting of a suture, a tape, a suture tape, a weave, a mesh, and combinations thereof.

In a further non-limiting embodiment of any of the foregoing methods, the reinforcement material is absorbable.

In a further non-limiting embodiment of any of the foregoing methods, at least one fixation device is attached to the reinforced biological construct.

In a further non-limiting embodiment of any of the foregoing methods, the at least one fixation device is a knotless, self-locking, adjustable construct formed of a button/loop construct having a button and a flexible, adjustable loop connected to the button, the flexible, adjustable loop having an adjustable length, the flexible, adjustable loop having two ends, two splices and two adjustable independently-formed loops that are interconnected.

In a further non-limiting embodiment of any of the foregoing methods, stitching the reinforcement material includes whipstitching the reinforcement material to an end of the biological construct.

In a further non-limiting embodiment of any of the foregoing methods, the whipstitching includes passing the suture loop/needle construct through the reinforcement material and the end multiple times to create multiple stitches in the reinforcement material and the end and after the last pass of the suture loop/needle construct through the end, passing one limb of a continuous suture loop of the suture loop/needle construct through each side of the biological construct.

In a further non-limiting embodiment of any of the foregoing methods, the reinforced biological construct is attached to a suture loop/button construct.

In a further non-limiting embodiment of any of the foregoing methods, attaching the reinforced biological construct to the suture loop/button construct includes looping the reinforced biological construct over a suture loop of the suture loop/button construct.

A method of reinforcing a biological construct according to another exemplary aspect of the present disclosure includes, among other things, fixedly attaching a suture loop/needle construct to a reinforcement material and after fixedly attaching the suture loop/needle construct to the reinforcement material, whipstitching the reinforcement material to a graft to form a reinforced graft construct using the suture loop/needle construct.

In a further non-limiting embodiment of the foregoing methods, the suture loop/needle construct includes a continuous suture loop.

In a further non-limiting embodiment of either of the foregoing methods, the continuous suture loop is fixedly attached to the reinforcement material.

In a further non-limiting embodiment of any of the foregoing methods, the continuous suture loop of the suture loop/needle construct is swedged to the reinforcement material.

In a further non-limiting embodiment of any of the foregoing methods, the continuous suture loop of the suture loop/needle construct is knotted to the reinforcement material.

In a further non-limiting embodiment of any of the foregoing methods, the method includes clamping the reinforcement material to the graft prior to whipstitching the reinforcement material to the graft.

In a further non-limiting embodiment of any of the foregoing methods, the method includes aligning a distal aspect of the reinforcement material to a distal aspect of the graft prior to whipstitching the reinforcement material to the graft.

In a further non-limiting embodiment of any of the foregoing methods, the method includes connecting the reinforced graft construct to a button/loop construct.

In a further non-limiting embodiment of any of the foregoing methods, the method includes connecting the reinforcement material to a fixation device prior to whipstitching the reinforcement material to the graft.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION OF THE PREFERRED EMBODIMENTS

Figure 1:
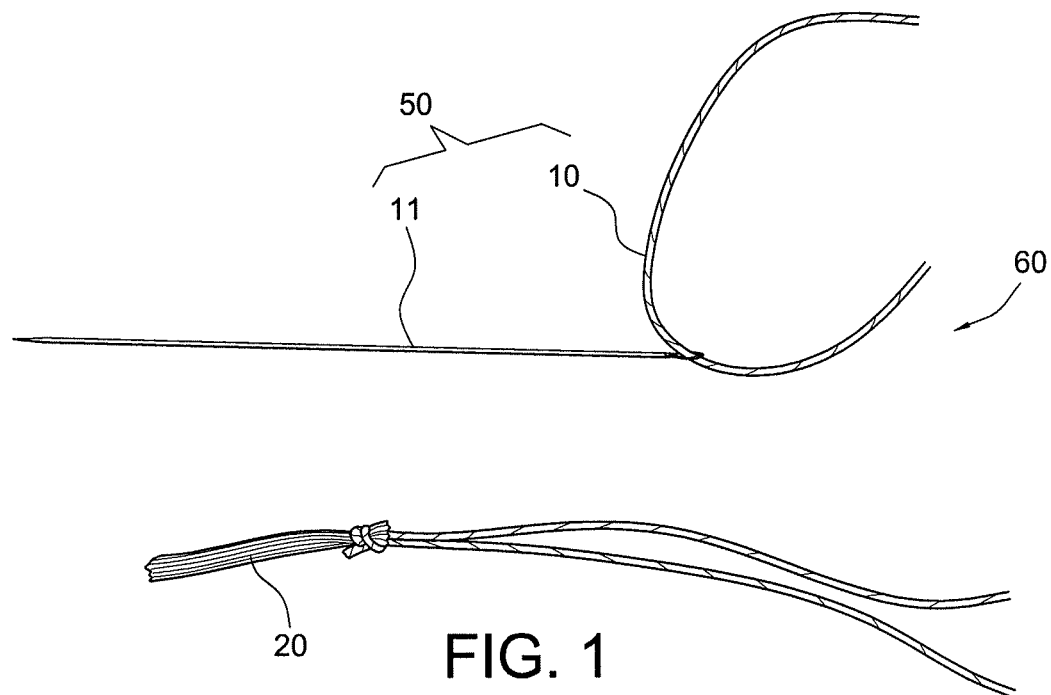
FIG. 1 illustrates an exemplary reinforcement construct (suture loop/needle construct with attached reinforcement material) of the present disclosure.

The present disclosure details surgical constructs and methods for tissue to bone repair employing a tissue construct reinforced with a reinforcement (reinforcing) material such as suture, tape, weave or mesh, among many others. The tissue construct may be any biological construct (for example, graft, ligament or tendon construct) that is employed for repairing a tendon or ligament, or similar anatomical structure. The construct may be attached to any fixation device(s) and/or to any bone tunnel(s).

In an exemplary-only embodiment, the reinforcement construct is in the form of a wide "tape like" material provided, on one end, with a loop that can be attached to a fixation device (for example, a RetroButton® (U.S. Patent Application Publication No. 2008/0046009), ACL Tightrope® (U.S. Pat. No. 8,460,379) or other suture loop/button construct). The wide "tape like" area is placed over the tendon or ligament and permits the surgeon to include the construct into the tendon/ligament stitches. The "tape like" material may include suture, Fiberwire® (U.S. Pat. No. 6,716,234), FiberTape® (U.S. Pat. No. 7,892,256), absorbable suture, tape, weave, or mesh, or any other material or combination of such materials. The "tape like" material is provided on the ligament or tendon, along a length thereon, and whipstitched to provide additional fixation when the ligament or tendon is implanted. The material may be absorbable or non-absorbable.

Preferably, the length of the construct approximates the length of the tendon or ligament that would normally be stitched.

In an exemplary embodiment, the construct is attached to a fixation device such as an exemplary ACL TightRope® or other button/suture loop construct. Attachment may be conducted simultaneously with the formation of the fixation device or may be conducted after the formation of the fixation device (i.e., the construct could be added secondarily to the fixation device).

The reinforced tissue constructs preferably include a stitched region formed by employing a suture loop construct with (1) a free floating needle that is attached to a continuous suture loop, and also with (2) a piece of material attached to the continuous suture loop. As detailed below, the piece of material is attached/affixed to at least a portion of the tissue (graft, ligament or tendon) to reinforce the tissue. The material may be any reinforcement (reinforcing) material such as suture, tape, weave, or mesh that can be attached (sutured) to the tissue. In an exemplary-only embodiment, the material is a suture tape such as FiberTape® (U.S. Pat. No. 7,892,256) manufactured by Arthrex, Inc. Naples, Fla., or a collagen tape, or a combination of these materials. The material may be attached to the tissue by suturing (for example, stitching such as whipstitching) or by any other affixing/attachment techniques, to provide additional fixation when implanted.

The reinforcing material may be bioabsorbable such that it will resorb away after a period of time in the body. The reinforced tissue (graft, ligament or tendon) construct may also be formed into a loop with at least one fixation device attached to the reinforced graft construct for various repairs such as ACL repairs. Tissue may be also directly attached to a fixation device, for example, a TightRope® construct (or other adjustable loops with button constructs) using the reinforcing material and attachment/suturing technique of the present disclosure.

The present disclosure also provides methods of forming reinforced tissue constructs having increased pull-out strength as well as methods of securing such reinforced tissue constructs in bone tunnels or sockets. An exemplary method of forming a reinforced tissue construct (reinforced biologic construct) according to the present disclosure comprises inter alia the steps of: (i) providing one or more tissue strands; and (ii) suturing/stitching at least a portion of the tissue strand(s) employing a suture loop/needle construct having a material attached to the suture loop/needle construct.

Referring now to the drawings, where like elements are designated by like reference numerals, FIGS. 1-31 illustrate exemplary surgical constructs 60, 160, 260, 360 of the present disclosure and methods of forming reinforced tissue constructs 99, 199, 299, 399 with such surgical constructs 60, 160, 260, 360.

Surgical construct 60 of FIG. 1 comprises a flexible suture loop/needle construct 50 with an attached piece of material 20. The flexible suture loop/needle construct 50 may be a construct similar to the FiberLoop® construct detailed and disclosed in U.S. Pat. No. 8,298,284 issued on Oct. 30, 2012, the disclosure of which is incorporated by reference herein in its entirety.

As detailed in U.S. Pat. No. 8,298,284, the suture loop/needle construct 50 includes a continuous loop of suture 10 (preferably a continuous loop of #2 FiberWire® suture (U.S. Pat. No. 6,716,234), sold by Arthrex, Inc. of Naples, Fla.) with both ends attached to a free floating thin needle 11 (such as a thin nitinol needle). The thin needle 11 is preferably straight and easy to handle, without instruments. The needle 11 moves freely on the suture loop 10 to recenter itself after passing through tissue and to facilitate even tensioning. The free floating needle 11 is not swaged on the suture loop 10 so, after passing the suture loop construct through the tissue to be treated, the needle may be recentered if the suture strands are uneven.

Surgical construct 60 is formed of suture loop/needle construct 50 with material 20 attached to the continuous suture loop 10. Material 20 may be any reinforcement/reinforcing material that can be attached (sutured) to the tissue (tendon/graft/ligament). In exemplary only embodiments, the material may be suture, tape, weave, or mesh, or any combinations of these materials. The material 20 may be suture tape such as FiberTape® (as disclosed in U.S. Pat. No. 7,892,256) or collagen tape, or combinations thereof. The material 20 may be bioabsorbable such that it will resorb away after a period of time in the body, or may be provided with various medicinal or therapeutic agents, for example, antiseptics, antibiotics, drugs, pharmaceutical agents, hormones and growth materials (for example, autogenous growth factors such as platelet-rich plasma (PRP), autologous factors, autologous-conditioned plasma (ACP)), among many others).

Figure 2:
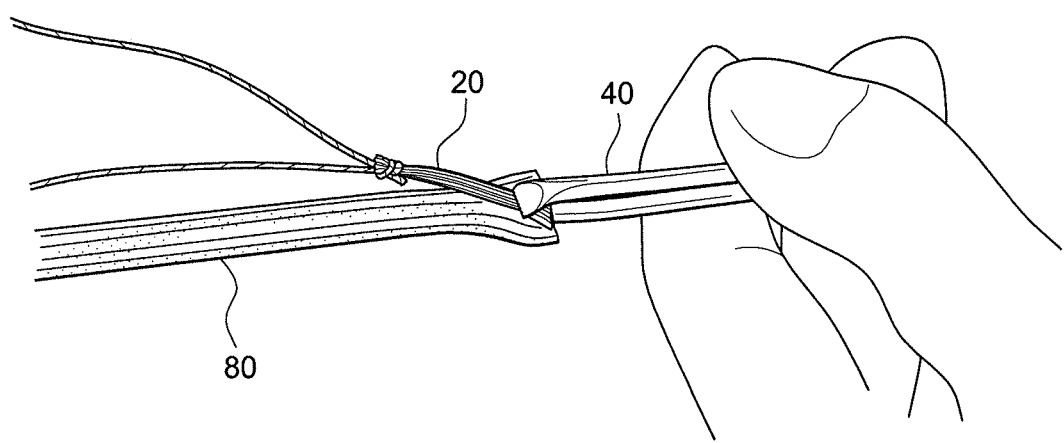
FIGS. 2-4 illustrate subsequent steps of a method of preparing a reinforced graft with the construct of FIG. 1, and according to an exemplary embodiment of the present disclosure.

The material may have any shape and geometry that provides reinforcement to the tissue to be sutured. For example, and according to an exemplary-only embodiment, the material may have a rectangular configuration (as shown in FIGS. 1 and 2) with a length of about 22.5 mm, or any configuration as long as it provides a surface area on which suturing/stitching may be conducted. The material may be provided in any length/width and then cut depending upon the configuration and geometry of the tissue (graft) to be reinforced.

FIG. 1 illustrates construct 60 with an exemplary 22.5 mm length of FiberTape® 20 swedged on to the FiberLoop® 10. Material 20 could be standard suture tape such as Fiber-Tape® or a collagen suture tape. In addition, the tape (for example, FiberTape®) could be provided longer and/or wider to allow the surgeon to cut it to the desired length and/or width, depending on the area of attachment (suturing or whipstitching). Material 20 may be attached to the continuous suture loop 10 by any method known in the art, for example, by swedging or knotting.

FIG. 2 illustrates material 20 disposed over tissue 80 (for example, graft or tendon 80 or any soft tissue). The distal aspect of material 20 is aligned with the distal aspect of the graft 80 and held in place with a clamp 40 (for example, an Alice clamp).

Figure 3:
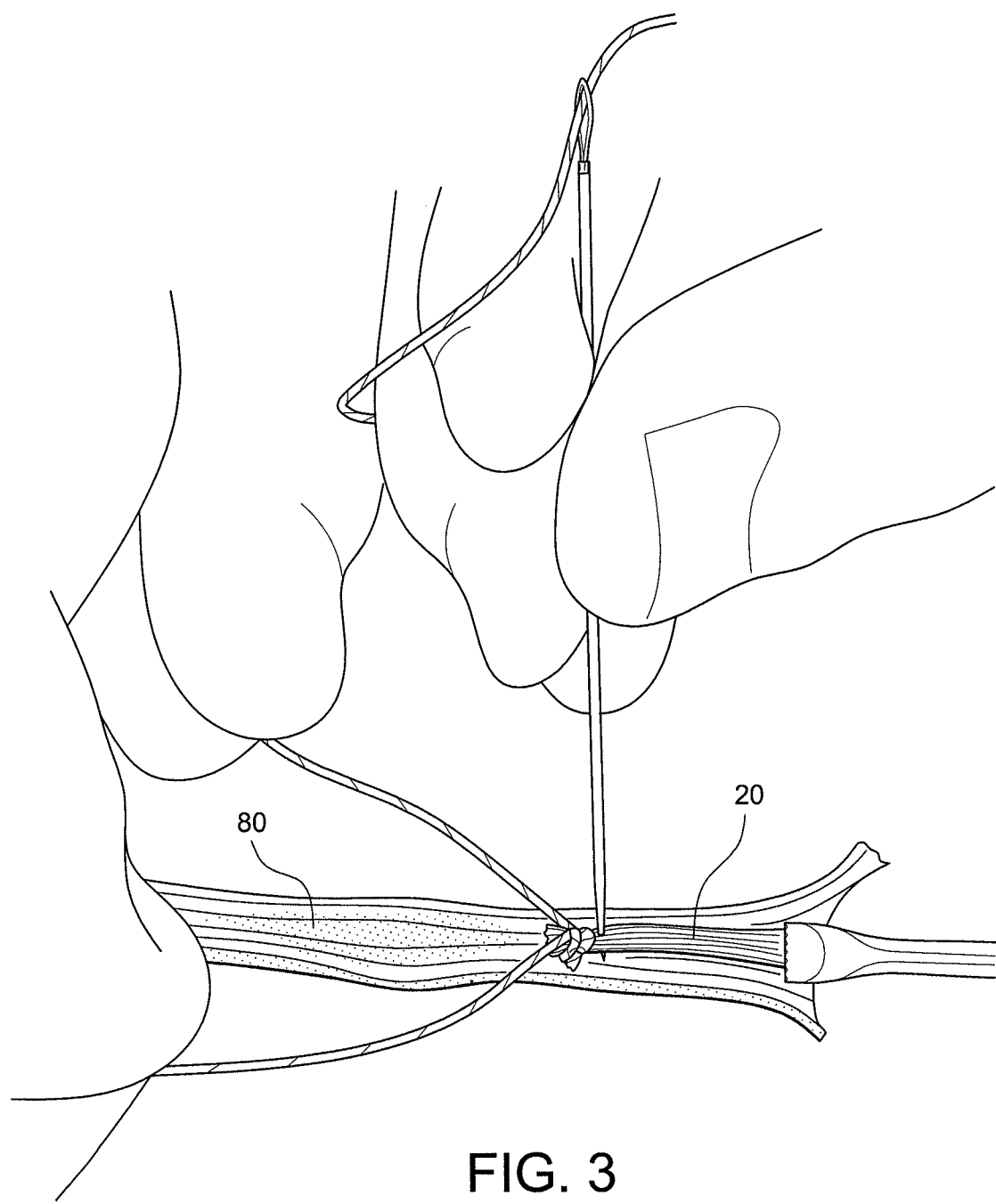

FIG. 3 shows secure attachment of the material 20 to the graft 80 by, for example, stitching (for example, whipstitching) the graft by piercing the material 20 with each step. Details of a method of stitching with a continuous suture loop with a free floating needle attached to it (such as FiberLoop® system 50) are set forth in U.S. Pat. No. 8,298,284, the entire disclosure of which is incorporated by reference in its entirety herewith.

Figure 4:
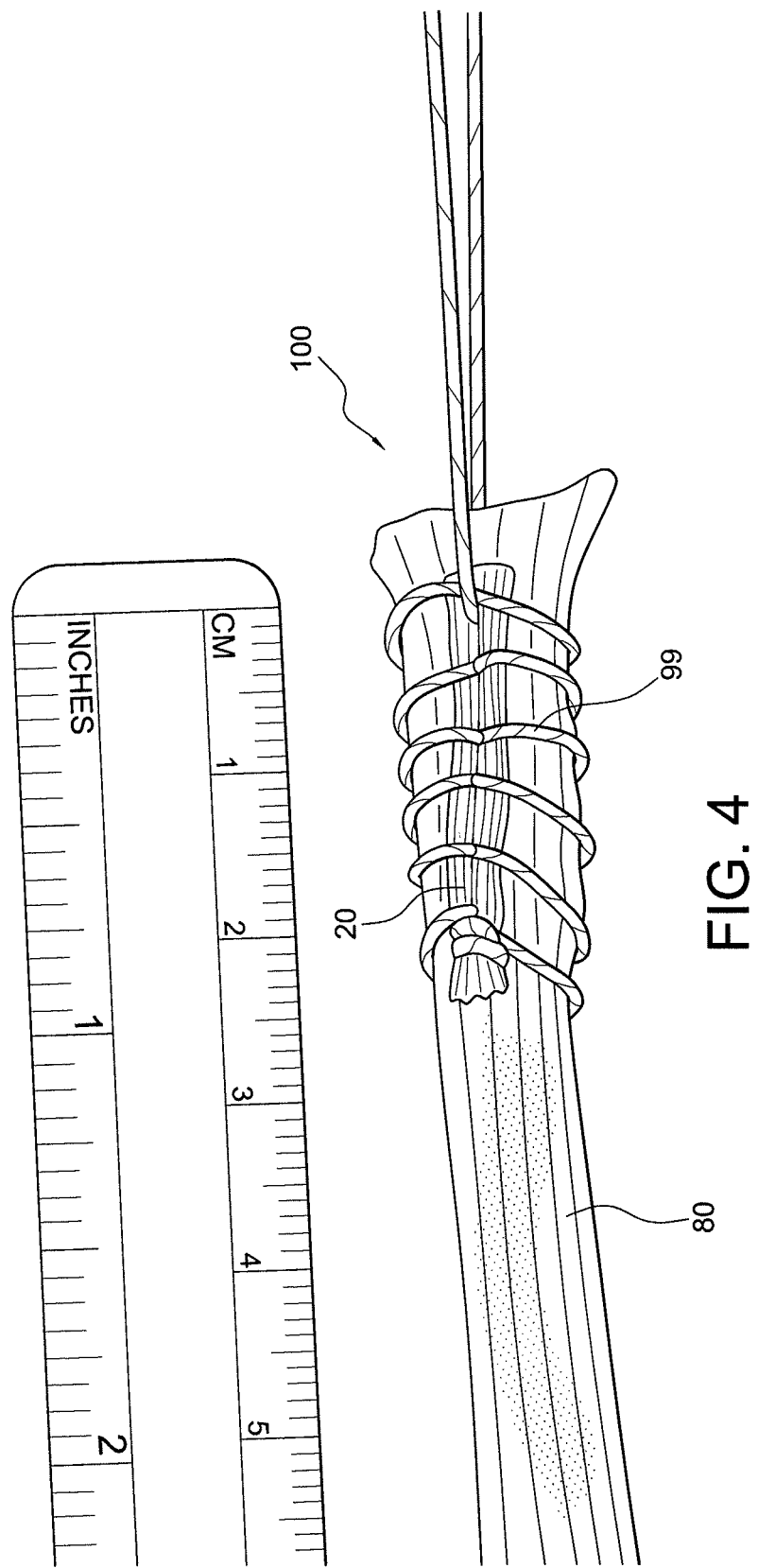

FIG. 4 illustrates how the FiberLoop® is passed through without having to double-back to form exemplary reinforced graft construct 99. After the last pass, one limb of the suture is brought back through the FiberTape® such that each suture limb is on either side of the graft. This allows the surgeon to pull the graft in-line with itself. This allows for a much stronger construct and much less suture bulk, which in turn, allows for smaller graft tunnels.

Figure 5:
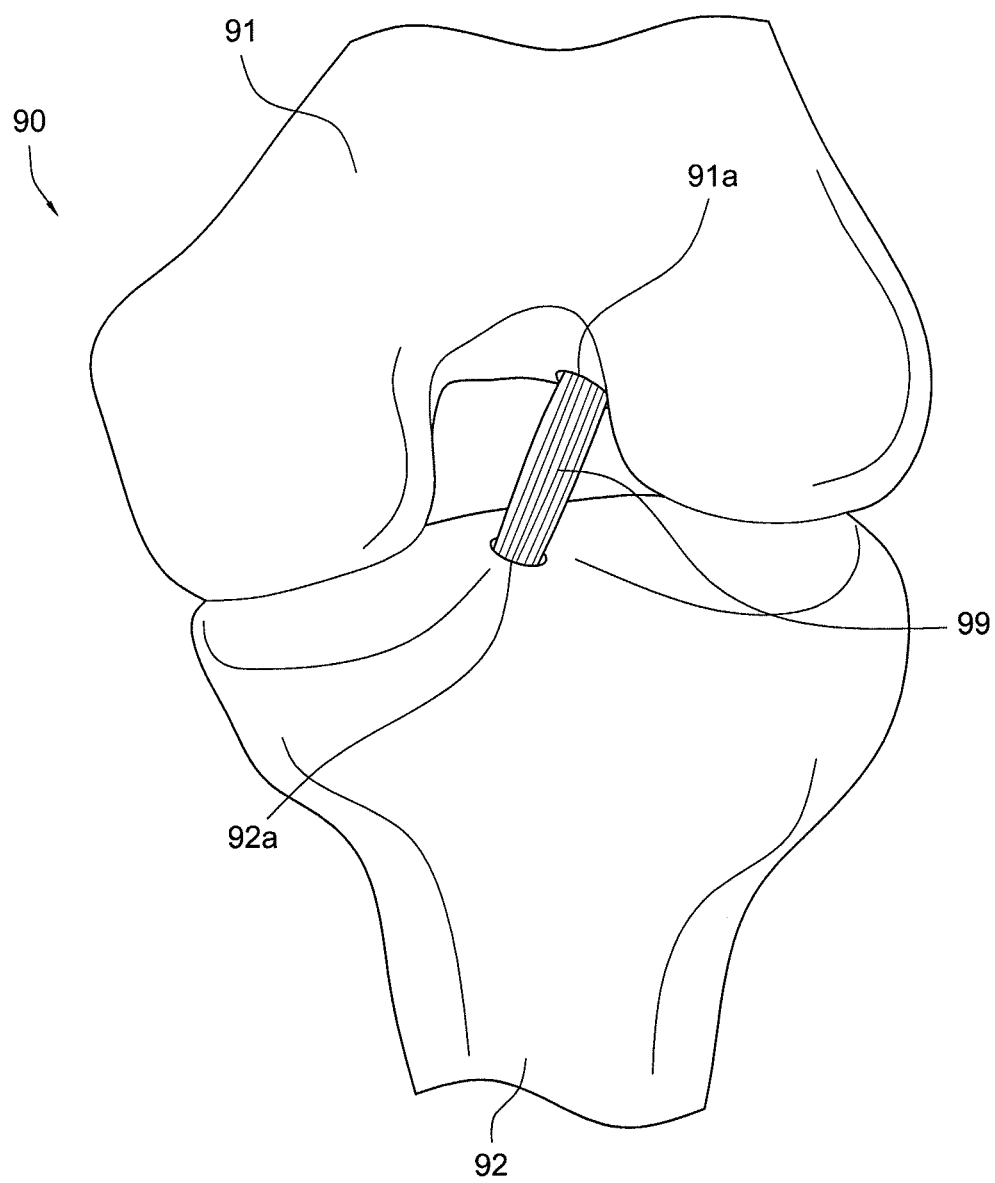
FIG. 5 illustrates the reinforced graft construct of FIG. 4 employed in ACL reconstruction and according to an exemplary method of the present disclosure.

FIG. 5 illustrates a schematic view of a knee 90 undergoing ACL reconstruction employing the reinforced graft construct 99 formed according to an embodiment of the present disclosure. Graft construct 99 is secured within femoral and tibial tunnels (sockets) 91a, 92a, each formed in femur 91 and tibia 92, respectively.

The femoral and tibial tunnels (sockets) 91a, 92a may be formed by a known technique, or alternatively, by using a retrodrill technique. According to the retrodrill technique, the tibial or femoral sockets are prepared by employing a retrodrill device provided with a retrodrill cutter detachable from a retrodrill guide pin, in the manner described in U.S. Pat. No. 7,238)89, issued Jul. 3, 2007, entitled "ACL Reconstruction Technique Using Retrodrill," the entire disclosure of which is incorporated by reference herein in its entirety.

Preferably, the step of securing the reinforced graft construct 99 in at least the tibial and femoral sockets or tunnels may be accomplished by plugging the target tunnel with a synthetic plug, bone plug or screw to contain and secure the reinforced graft construct 99 in the tunnel or, alternatively, by employing knotless lateral fixation using, for example, two knotless fixation devices (such as interference screws or graftbolt-type fixation devices). The fixation devices may be preferably formed of a translucent or transparent polymer material, preferably bioabsorbable materials such as polyglycolic or polylactic acid polymers.

According to yet another embodiment, graft insertion and fixation may be conducted by employing a continuous loop/button construct provided with a button, preferably of titanium alloy, and a continuous loop attached to the button. The button has an oblong configuration and a width that is preferably less than about 1mm narrower than the width of the drill hole through which the button is inserted and subsequently passed through. The button is provided with an inside eyelet that allows the passage of the continuous loop. In an exemplary embodiment, the suture loop may be a single high strength suture such as FiberWire® suture. In another exemplary embodiment, the continuous loop may be formed of a plurality of suture strands configured to separate from a single strand to a plurality of strands in a continuous loop. In yet another embodiment, the loop is an adjustable loop (forming a TightRope® ACL construct) which consists of two interconnected, adjustable flexible loops formed by splicing a suture strand in a manner disclosed in U.S. Pat. No. 8,439,976 issued on May 14, 2013 and U.S. Pat. No. 8,460,379 issued on Jun. 11, 2013, the disclosures of both of which are incorporated by reference in their entireties herein.

When employing an adjustable button/loop construct such as the suture loop/button construct disclosed in U.S. Pat. Nos. 8,439,976 and 8,460,379 (comprising an adjustable loop formed of two interconnected loops (two eyesplice loops) and two splices), the tissue may be attached directly to the adjustable button/loop construct using the suturing technique of the present disclosure (i.e., using surgical construct 60 to secure material 20 to tissue while suturing the tissue). The tissue is looped over the adjustable loop of the button/suture loop construct and then secured to it by employing construct 60 with material 20 attached to the continuous loop of suture 10. Securing the two ends of the tissue to the adjustable loop may be conducted in various ways, for example, by the methods and techniques disclosed in U.S. Publication No. 2012/0046746, the disclosure of which is incorporated herein in its entirety. The ends of the tissue (graft) to be reinforced may be brought together in an overlapping or non-overlapping manner, and then secured and reinforced by suturing/stitching with material 20 to the tissue.

FIGS. 6-10 illustrate a reinforced graft construct for repairing a tendon or ligament formed by attaching a piece of material (reinforcing material) having a general rectangular configuration to the graft lengthwise. An end of the material is provided with a loop or an eyelet to permit direct attachment to a fixation device, for example, to a suspensory fixation device such as a suture loop/button construct having a continuous flexible loop with an adjustable perimeter (for example, an ACL TightRope®).

Like in the previously-described embodiment, the material may be bioabsorbable such that it will resorb away after a period of time in the body. The graft (tendon or ligament) and the material are whip stitched together as is known in the art to provide for added strength of the graft for better fixation.

Figure 6:
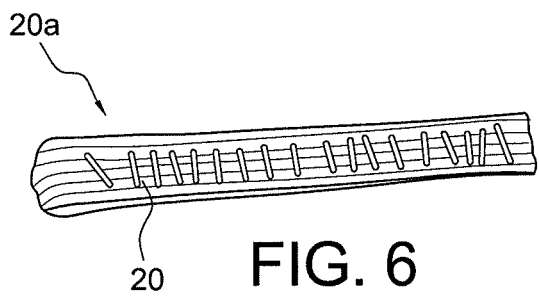
FIGS. 6 and 7 illustrate a top view and a side view, respectively, of another exemplary reinforcement construct of the present disclosure.
Figure 7:
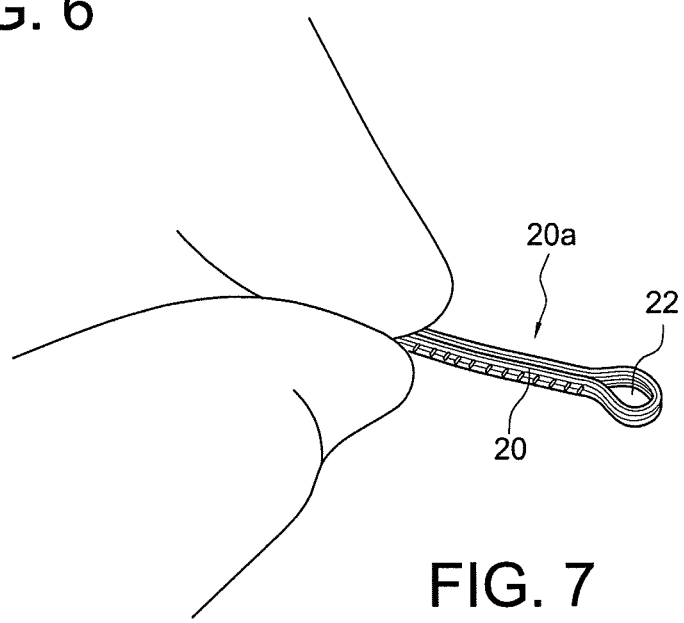

FIGS. 6 and 7 illustrate an exemplary construct 20a in the form of a wide "tape like" material 20 (reinforcing material 20) provided, on one end, with a loop 22 that can be attached to a fixation device. Preferably, the length of the construct approximates the length of the tendon/ligament/graft that will be stitched.

Figure 8:
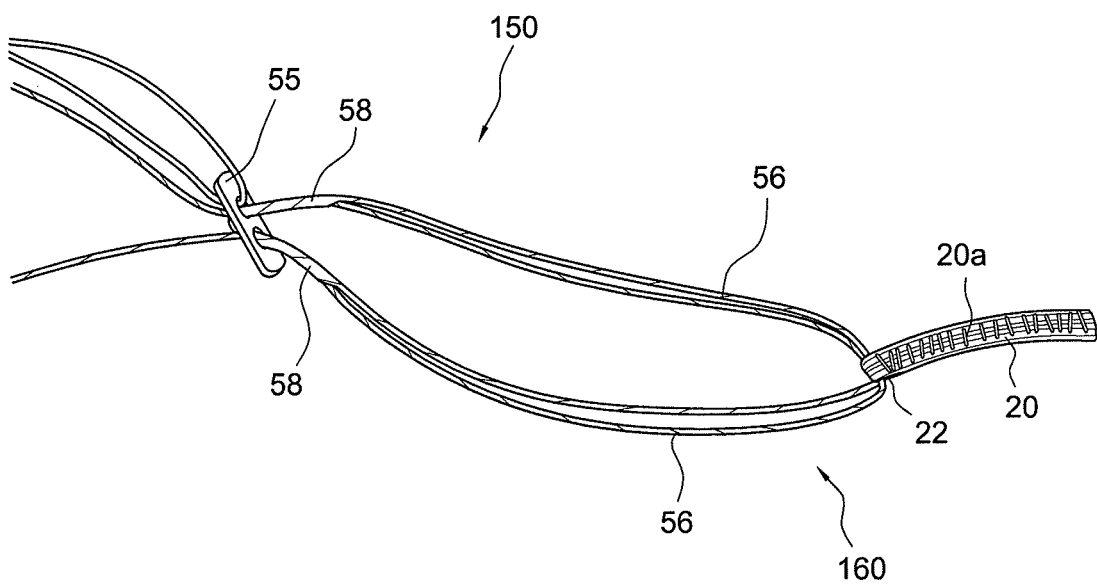
FIG. 8 illustrates the reinforcement construct of FIG. 7 attached to a fixation device (an exemplary ACL TightRope®) and according to an exemplary embodiment of the present disclosure.

FIG. 8 illustrates construct 20a attached to exemplary fixation device 150 in the form of an ACL TightRope® 150, to form assembly 160. Construct 20a can be provided pre-assembled to the adjustable, continuous, knotless loop of the fixation device 150 (pre-constructed with the loop 22 attached to the fixation device 150) or the construct 20a could be added secondarily to the fixation device.

The TightRope® ACL construct 150 is an adjustable knotless fixation device with a button 55 and two interconnected suture loops 56 forming two eyesplices 58, the loops being adjustable and connected to each other, and further attached to the button. The TightRope® ACL construct offers adjustable cortical fixation for cruciate ligament reconstruction (as a four-point knotless fixation that resists cyclic displacement and offers strong pull-out strength).

Figure 9:
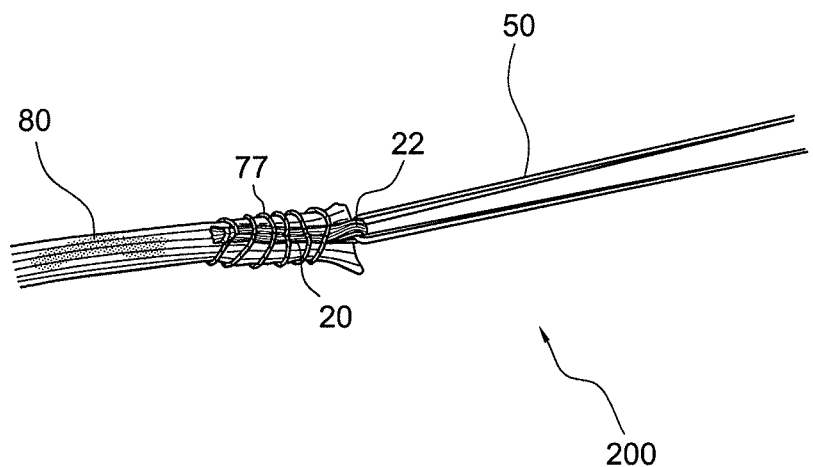
FIG. 9 illustrates the assembly of FIG. 8 attached to a tendon, ligament or graft (by whipstitching) to form a reinforced ligament or tendon construct (a top view).
Figure 10:
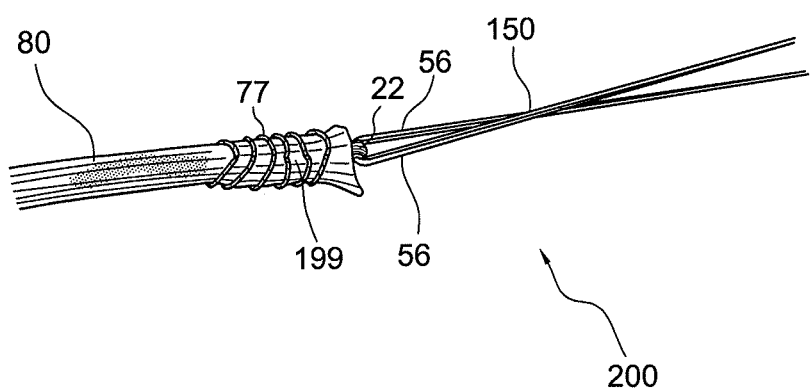
FIG. 10 illustrates the assembly of FIG. 8 attached to tissue (a tendon, ligament or graft) by whipstitching to form a reinforced ligament or tendon construct (a bottom view).
Figure 11:
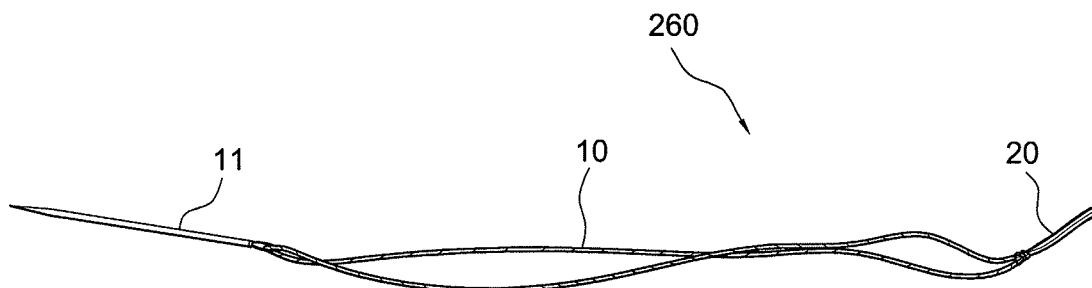
FIGS. 11 and 12 illustrate another exemplary reinforcement construct and assembly of the present disclosure.

FIGS. 9 and 10 illustrate assembly 160 attached to tendon/ligament/graft 80 to form reinforced graft assembly 200 (including reinforced graft construct 199).

The wide "tape like" area 20 (reinforcing material 20) of construct 20a is placed over the tendon/ligament/graft 80 and permits the surgeon to include the construct 20a into the tendon/ligament stitches 77. The "tape like" material 20 may include suture, FiberWire®, tape such as FiberTape®, absorbable suture, weave, or mesh, or any other material or combination of such materials that can be provided on the ligament or tendon, along a length thereon, and whipstitched to provide additional fixation when the ligament or tendon is implanted. The material 20 of construct 20a may be absorbable or non-absorbable.

Construct 20a of the present disclosure allows a straight tendon (that cannot be folded) to be connected to a suspensory fixation device such as the ACL TightRope®.

In one embodiment, assembly 200 may be used for an arthroscopic repair such as ACL repair. A variety of fixation devices for the tibia and/or femur may be attached to the loop 22 of construct 20a and for further attachment to a graft/ligament/tendon for ACL repair with fixation at either one or both ends (and prior to the loop formation). Examples of fixation devices include a loop with a button (such as the RetroButton® manufactured by Arthrex Inc.) or an adjustable loop with button (such as the ACL TightRope® manufactured by Arthrex Inc.).

Material 20 (reinforcing material 20) of construct 20a is stitched to the graft/ligament/tendon 80 using a needle and suture, for example, to whipstitch through the construct 20 and the graft/ligament/tendon 80, to create reinforced assembly 200 (reinforced graft, ligament or tendon loop construct 199 attached to a continuous loop/button suture construct). Once the whipstitching is completed, the reinforced assembly may be pre-tensioned to 20 pounds for use in ACL repair. The type of repair for which the construct is being used for will determine the amount of pre-tensioning, which may be up to 50 pounds.

Although the above method was described using whipstitching, any type of suturing/stitching that would attach construct 20a to graft/ligament/tendon 80 could be used. Additionally, the construct 20a attached to the graft/ligament/tendon 80 may be an absorbable suture tape that would resorb away after a length of time in the body.

Figure 12:
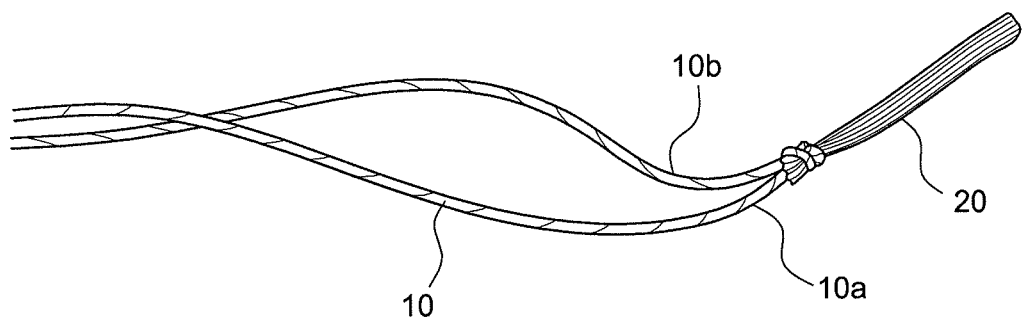

FIGS. 11-16 illustrate another construct and method of reinforcing soft tissue graft/ligament/tendon 80 using a FiberLoop® 10 with construct 20. FiberTape® 20 is attached to the FiberLoop® 10 with needle 11 through a plurality of tails/ends 10a, 10b, to form construct 260 as shown in FIG. 12. Material 20 could be standard suture tape such as FiberTape® or a collagen suture tape. In addition, the tape (for example, FiberTape®) could be provided longer and/or wider to allow the surgeon to cut it to the desired length and/or width, depending on the area of attachment (suturing or whipstitching). Material 20 may be formed as part of the continuous suture loop 10.

Figure 13:
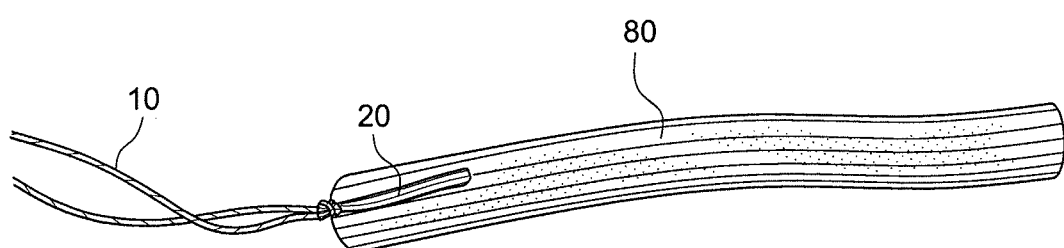
FIGS. 13-16 illustrate exemplary steps of a method of attaching the reinforcement construct of FIG. 12 to tissue (tendon, ligament or graft).

FIG. 13 illustrates material 20 of construct 260 disposed over tissue 80 (for example, graft or tendon 80 or any soft tissue) for reinforced whipstitch technique. The FiberTape® portion is placed over the graft end to be stitched.

Figure 14:
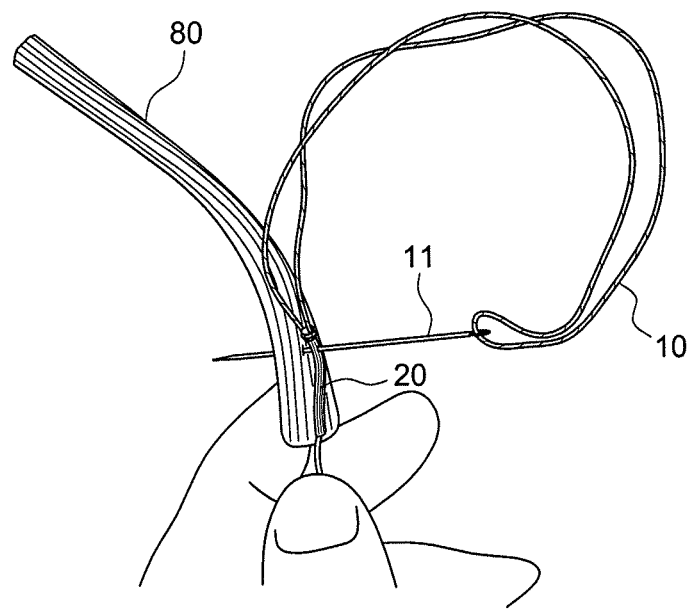
Figure 15:
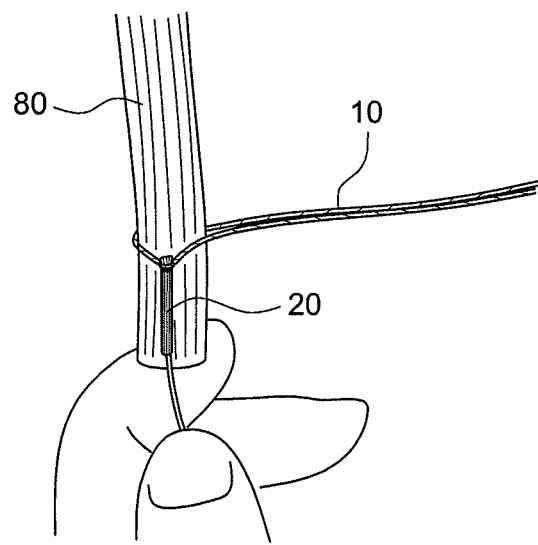
Figure 16:
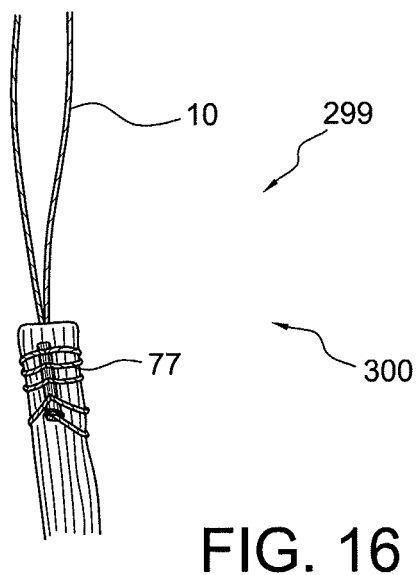

FIGS. 14-16 illustrate securing of material 20 to tissue 80 by stitching, for example, with the flexible strand of loop 10 to form reinforced construct 299 with stitching pattern 77. The graft 80 and the FiberTape® tail 20 are being stitched together with the FiberLoop® (FIG. 14). A complete first stitch is shown in FIG. 15 and the final soft tissue construct 299 reinforced with material 20 as part of assembly 300 (with suturing pattern 77) is shown in FIG. 16.

Figure 17:
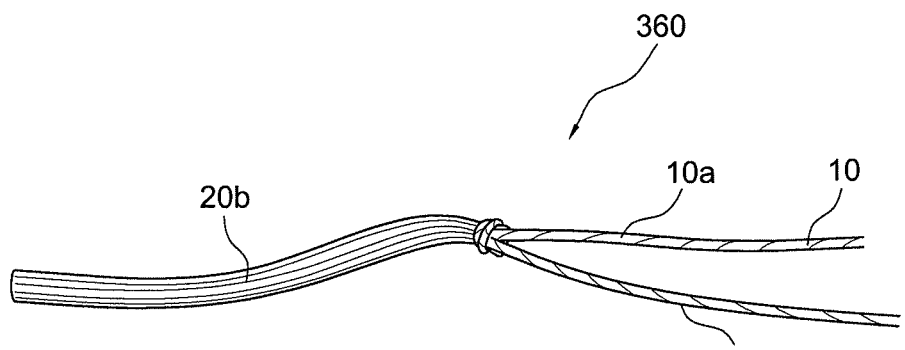
FIG. 17 illustrates another exemplary reinforcement construct and assembly of the present disclosure.

FIGS. 17-22 illustrate another construct 360 and method of reinforcing soft tissue graft/ligament/tendon 80 using a longer reinforcement material 20b which is also part of FiberLoop® 10 through ends/splices 10a, 10b, as shown in FIG. 17.

Figure 18:
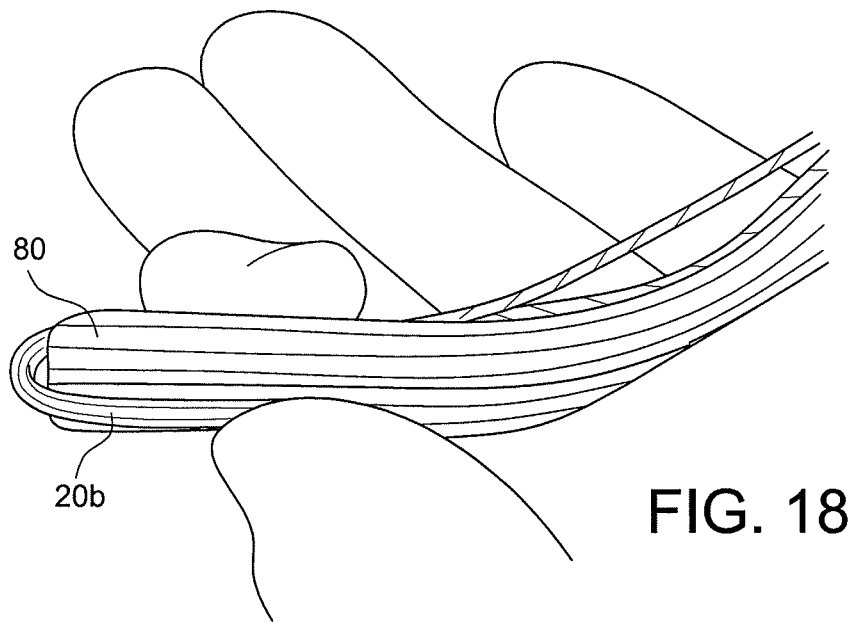
FIGS. 18-22 illustrate exemplary steps of a method of attaching the reinforcement construct of FIG. 17 to tissue (tendon, ligament or graft).
Figure 19:
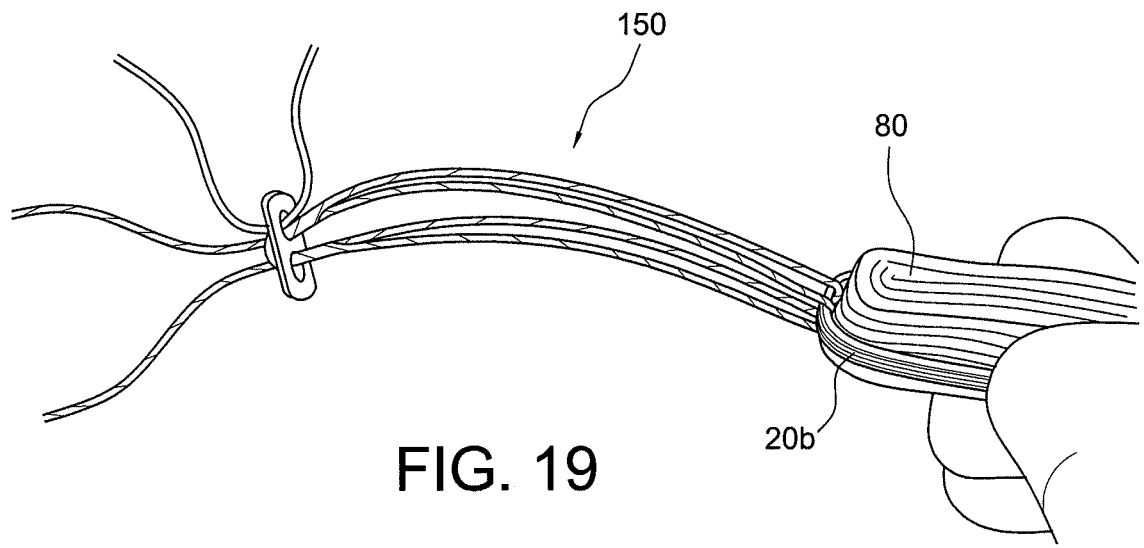
Figure 20:
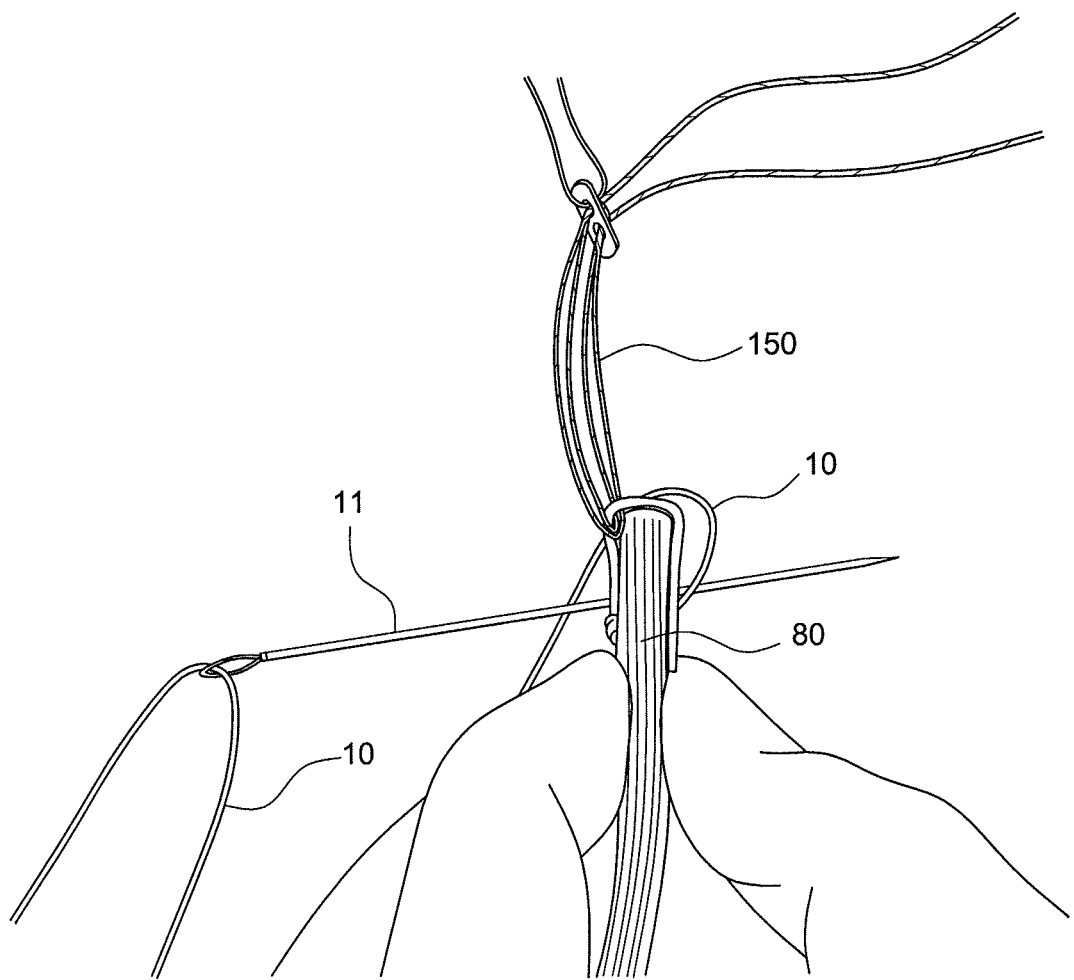
Figure 21:
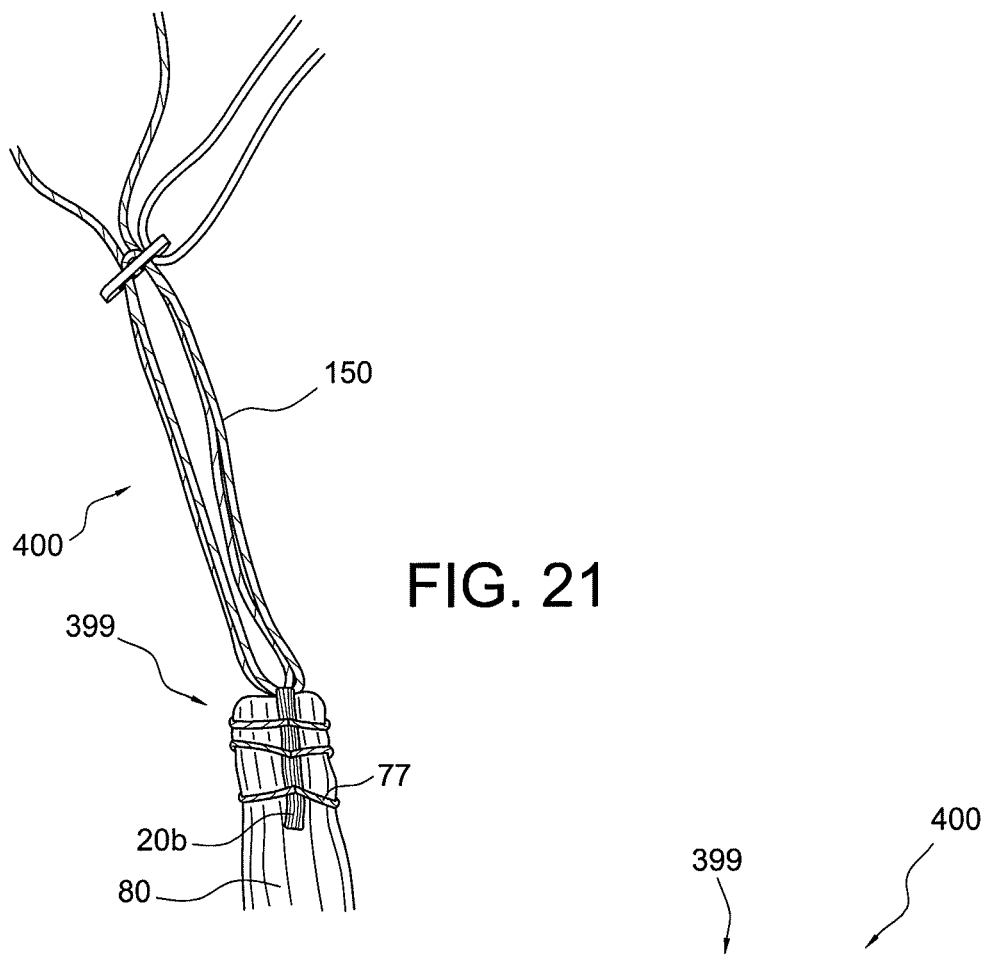
Figure 22:
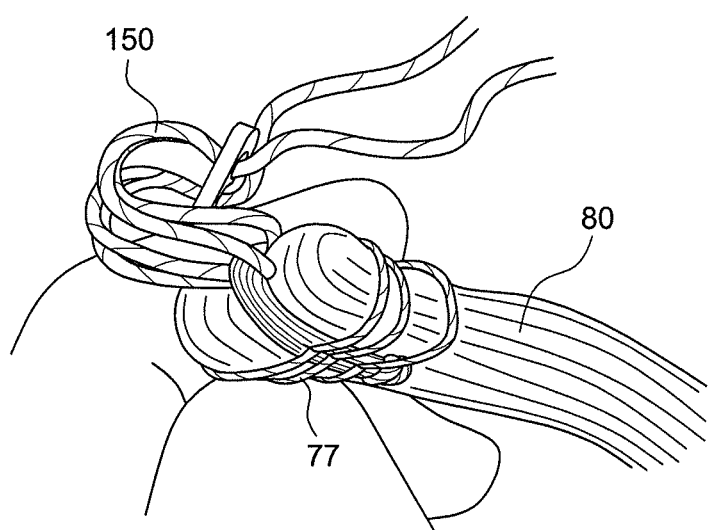

Longer FiberTape® 20b is folded over the graft 80, as shown in FIG. 18. Exemplary implant 150 (for example, an ACL TightRope® 150) is placed in the looped FiberTape® 20b (FIG. 19). A FiberLoop® stitch 77 is then placed through the graft 80 and folded FiberTape® 20b, as shown in FIG. 20. Completed reinforced graft construct 399 as part of assembly 400 is illustrated in FIGS. 21 and 22.

Figure 23:
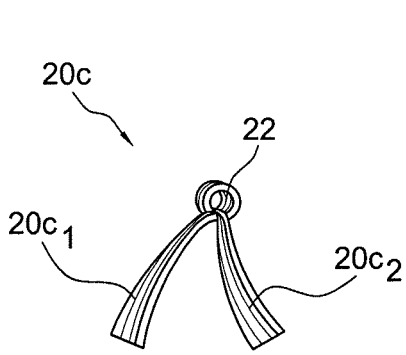
FIGS. 23-31 illustrate additional exemplary embodiments of reinforcement constructs and methods of attaching them to tissue (tendon, ligament or graft).
Figure 24:
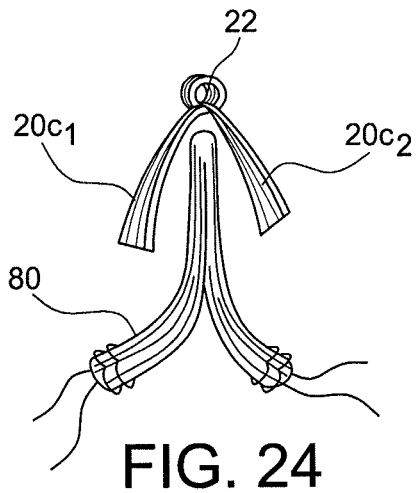
Figure 25:
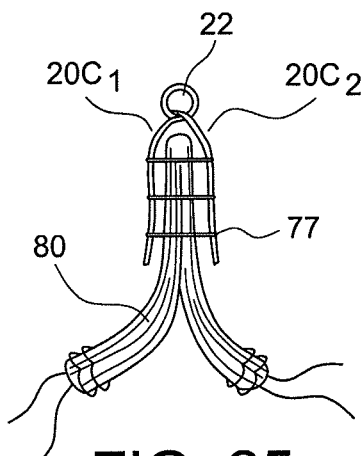

FIGS. 23-31 illustrate additional embodiments of constructs 20c, 20d, 20e, 20f, 20g, 20h for attachment to a graft/ligament/tendon 80. FIGS. 23-25 illustrates construct 20c with loop 22 and two suture tape tabs 20ci, 20c2 (FiberTape® tabs) that allow FiberTape® reinforcement on both sides of the graft/ligament/tendon 80. The graft/ligament/tendon is placed between tabs 20c1, 20c2 and then it is sutured (stitched) to the tabs 20ci, 20c2 with stitches 77.

Figure 26:
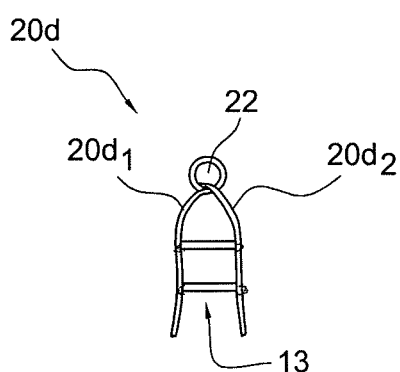
Figure 27:
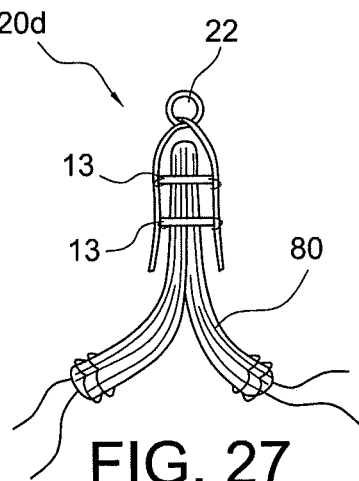

FIGS. 26 and 27 illustrate a two-ply construct 20d with circumferential connections 13. The connections 13 are provided between the tabs 20di, 20d2 to allow the construct 20d to slide over the graft/ligament/tendon 80 circumferentially (as shown in FIG. 27).

Figure 28:
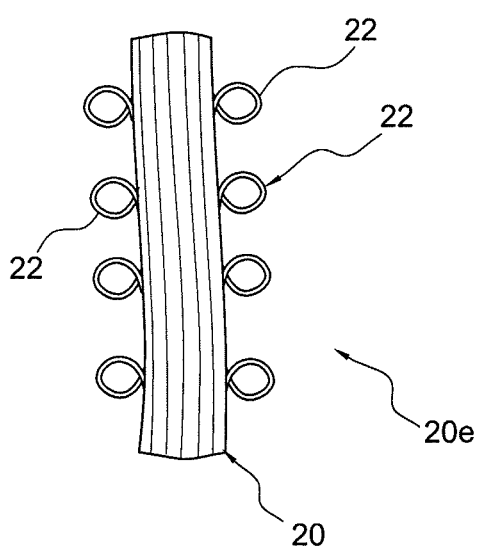

FIG. 28 illustrates construct 20e in the form of a length of FiberTape® with a plurality of external eyelets 22 used for suturing. External eyelets 22 may be provided in any number and may have any shape (similar and/or different). As shown in FIG. 28, external eyelets 22 are provided along at least two lengths of the FiberTape® 20, and/or around the perimeter of the FiberTape® 20.

Figure 29:
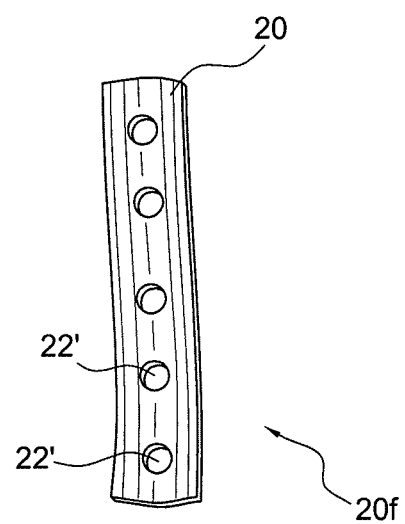

FIG. 29 illustrates construct 20f in the form of a length of FiberTape® with a plurality of internal eyelets 22' used for suturing. Internal eyelets 22' are provided within the body of the FiberTape® 20, at symmetrical or non-symmetrical positions.

Figure 30:
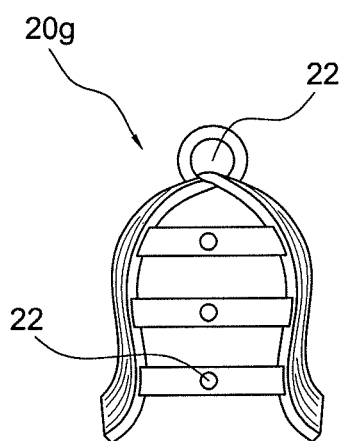
Figure 31:
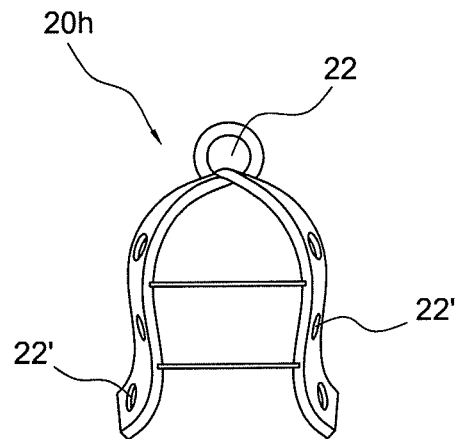

FIGS. 30 and 31 illustrate additional constructs 20g, 20h with eyelets 22, 22' and connections 13, and according to other embodiments of the present disclosure.

Although some of the embodiments above have been described with reference to attachment of the reinforced tissue to a specific button/loop construct (such as an ACL TightRope®, for example), it must be understood that the disclosure is not limited to these exemplary-only embodiments. Accordingly, the present disclosure also contemplates attachment of the reinforced tissue (reinforced with material 20 of surgical construct 60, 160, 260, 360) to any device (e.g., any type of fixation device) or a bone tunnel.

The present disclosure further provides methods of ligament reconstruction employing reinforced tissue constructs. An exemplary method of the present disclosure comprises inter alia the steps of: (i) providing a target tunnel for ligament reconstruction; (ii) providing a stitched reinforced tissue construct comprising at least a reinforced stitched region, the reinforced stitched region including a reinforcement (reinforcing) material located between tissue (tendon/ligament/graft) and the stitching; (iii) inserting the stitched tissue construct into the target tunnel; and (iv) securing the stitched tissue construct in the tunnel.

Reinforcement material 20 may consist essentially of suture or suture material, or of combination of suture and other materials such as long chain synthetic polymers like polyester and nylon, or materials such as PET, silk nylon or absorbable polymers, or coating materials (such as wax, silk, or silicone products), among many others. These materials augment the strength and pliability of the construct, and improve the characteristics and properties of the suture material.

The suture forming the continuous loop 10 attached to material 20 may be formed of any flexible material. In the preferred embodiment, the sutures are formed of a high strength suture material such as FiberWire® suture, sold by Arthrex, Inc. of Naples, Fla., and described in U.S. Pat. No. 6,716,234, the disclosure of which is incorporated by reference herein. The high strength suture may be available in various lengths and, preferably, is a #2 FiberWire® suture strand. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material.

While the present embodiments are described herein with reference to illustrative figures for particular applications, it should be understood that the embodiments are not limited thereto. Those having ordinary skill in the art and access to the teachings provided herein, will recognize additional modifications, applications, embodiments and substitution of equivalents all falling within the scope of the presented embodiments.

What is claimed is:

1. An assembly, comprising:
   a fixation device including a button and an adjustable loop attached to the button, wherein the adjustable loop includes a first adjustable loop forming a first eyesplice and a second adjustable loop interconnected with the first adjustable loop and forming a second eyesplice; and
   a construct including a wide tape-like reinforcing material attached to the adjustable loop,
   wherein the wide tape-like reinforcing material includes a plurality of adjacent stitches,
   wherein the wide tape-like reinforcing material is configured to be attached to a biological construct by a plurality of whipstitches, wherein the plurality of whipstitches are separate stitches from the plurality of adjacent stitches.

2. The assembly as recited in claim 1, wherein the button is a cortical fixation button.

3. The assembly as recited in claim 1, wherein the button is a metallic button.

4. The assembly as recited in claim 3, wherein the metallic button is a titanium alloy button.

5. The assembly as recited in claim 1, wherein the construct includes a loop configured to receive the adjustable loop.

6. The assembly as recited in claim 5, wherein an interconnection between the first adjustable loop and the second adjustable loop is received within the loop of the construct.

7. The assembly as recited in claim 1, wherein the construct is configured to be attached to athe biological construct such that a distal edge of a distal end of the construct is aligned to be even with a distal edge of a distal end of the biological construct.

\* \* \* \* \*